(12) United States Patent
Lin et al.

(10) Patent No.: US 11,083,414 B2
(45) Date of Patent: Aug. 10, 2021

(54) SYSTEM AND METHOD FOR HEALTH CONDITION MONITORING

(71) Applicants: Delta Electronics Int'l (Singapore) Pte Ltd, Singapore (SG); Nanyang Technological University, Singapore (SG)

(72) Inventors: Zhiping Lin, Singapore (SG); Yongkiang Yeo, Singapore (SG); Jianmin Zhang, Singapore (SG); Wee Ser, Singapore (SG); Yenpo Tai, Singapore (SG)

(73) Assignees: DELTA ELECTRONICS INT'L (SINGAPORE) PTE LTD, Singapore (SG); NANYANG TECHNOLOGICAL UNIVERSITY, Singapore (SG)

( * ) Notice: Subject to any disclaimer, the term of this patent is extended or adjusted under 35 U.S.C. 154(b) by 243 days.

(21) Appl. No.: 16/171,685

(22) Filed: Oct. 26, 2018

(65) Prior Publication Data
US 2019/0125263 A1 May 2, 2019

(30) Foreign Application Priority Data
Oct. 30, 2017 (SG) .............. 10201708876V

(51) Int. Cl.
*A61B 5/00* (2006.01)
*A61B 5/08* (2006.01)
(Continued)

(52) U.S. Cl.
CPC ............ *A61B 5/6805* (2013.01); *A61B 5/002* (2013.01); *A61B 5/0205* (2013.01);
(Continued)

(58) Field of Classification Search
CPC . A61B 5/6805; A61B 5/04525; A61B 5/0408; A61B 5/002; A61B 5/0205;
(Continued)

(56) References Cited

U.S. PATENT DOCUMENTS

| 2008/0074307 A1* | 3/2008 | Boric-Lubecke ....... G01S 13/56 342/28 |
| 2011/0137209 A1* | 6/2011 | Lahiji .................... A61B 7/026 600/586 |

(Continued)

FOREIGN PATENT DOCUMENTS

| JP | 2016173713 A | 9/2016 |
| WO | 2011/117862 A2 | 9/2011 |

(Continued)

OTHER PUBLICATIONS

Chien-Lung Shen et al., Respiratory Rate Estimation by Using ECG, Impedance, and Motion Sensing in Smart Clothing, J. Med. Biol. Eng., 2017, 37:826-842, Springer.

(Continued)

*Primary Examiner* — Gary Jackson
*Assistant Examiner* — Sebastian X Lukjan
(74) *Attorney, Agent, or Firm* — Kirton McConkie; Evan R. Witt

(57) ABSTRACT

A system for health condition monitoring includes a wearable device, a portable device and a server. The portable device is capable of communicating between the wearable device and the server. The system further includes a non-contact ECG acquisition module for capturing ECG signals from a user wearing the wearable device, a non-contact audio acquisition module for capturing a respiratory sound signal and a heart sound signal from the user wearing the wearable device, a first signal processing and analysis module for receiving and processing the ECG signals, the (Continued)

respiratory sound signal and the heart sound signal to perform QRS detection, HR calculation and ECG derived RR determination, and a second signal processing and analysis module for receiving and processing the ECG signals, the respiratory sound signal and the heart sound signal to perform heart sound localization, heart sound cancellation, respiratory sound restoration, and sound based RR determination.

31 Claims, 14 Drawing Sheets

(51) Int. Cl.
 A61B 5/25 (2021.01)
 A61B 5/35 (2021.01)
 A61B 5/349 (2021.01)
 A61B 5/0205 (2006.01)
 A61B 7/00 (2006.01)
 A61B 5/0245 (2006.01)

(52) U.S. Cl.
 CPC .............. *A61B 5/0816* (2013.01); *A61B 5/25* (2021.01); *A61B 5/349* (2021.01); *A61B 5/35* (2021.01); *A61B 5/7203* (2013.01); *A61B 7/003* (2013.01); *A61B 5/0245* (2013.01); *A61B 5/7257* (2013.01); *A61B 5/7278* (2013.01); *A61B 2562/028* (2013.01); *A61B 2562/0209* (2013.01)

(58) Field of Classification Search
 CPC ..... A61B 5/0452; A61B 5/7203; A61B 7/003; A61B 5/0816; A61B 2562/0209; A61B 5/0245; A61B 5/7257; A61B 5/7278; A61B 2562/028; A61B 5/25; A61B 5/35; A61B 5/349
 See application file for complete search history.

(56) References Cited

U.S. PATENT DOCUMENTS

| 2011/0181422 A1* | 7/2011 | Tran ................ A61B 5/0022 340/573.1 |
| 2014/0148711 A1* | 5/2014 | Yang ................ A61B 7/003 600/484 |
| 2015/0065894 A1* | 3/2015 | Airaksinen ........ A61B 5/0816 600/484 |
| 2015/0265161 A1* | 9/2015 | Hernandez ........ A61B 5/024 600/476 |
| 2016/0051205 A1* | 2/2016 | Al-Ali ............... G16H 40/63 600/301 |
| 2016/0052205 A1 | 2/2016 | FrantzDale |
| 2016/0135708 A1* | 5/2016 | Chakravarthy .... A61B 5/04012 600/515 |
| 2017/0188972 A1* | 7/2017 | Banet ............... A61B 5/4872 |
| 2017/0202459 A1* | 7/2017 | Cao ................. A61B 5/0205 |

FOREIGN PATENT DOCUMENTS

| WO | WO-2011117862 A2 * | 9/2011 | ........ A61B 5/6804 |
| WO | WO-2015002945 A2 * | 1/2015 | ........ A61B 5/0464 |

OTHER PUBLICATIONS

T E Ayoob Khan, Separating Heart Sound from Lung Sound Using LabVIEW, International Journal of Computer and Electrical Engineering, vol. 2, No. 3, Jun. 2010, 524-533.

Yu M. Chi et al., Wireless Non-contact Biopotential Electrodes, Proceeding WH '10 Wireless Health, Oct. 5, 2010, pp. 194-195.

Noman Qaid Al-Naggar et al., Design of a Two-channel Instrument to Record Lung and Heart Sounds Simultaneously and Separate Them Using ANC-NLMS Algorithm, International Journal of Advanced Research in Electrical, Electronics and Instrumentation Engineering, vol. 4, Issue 4, Apr. 2015, 2601-2609.

European Search Report for European Application No. 18200030.7, "System and Method for Health Condition Monitoring," Jun. 24, 2019.

* cited by examiner

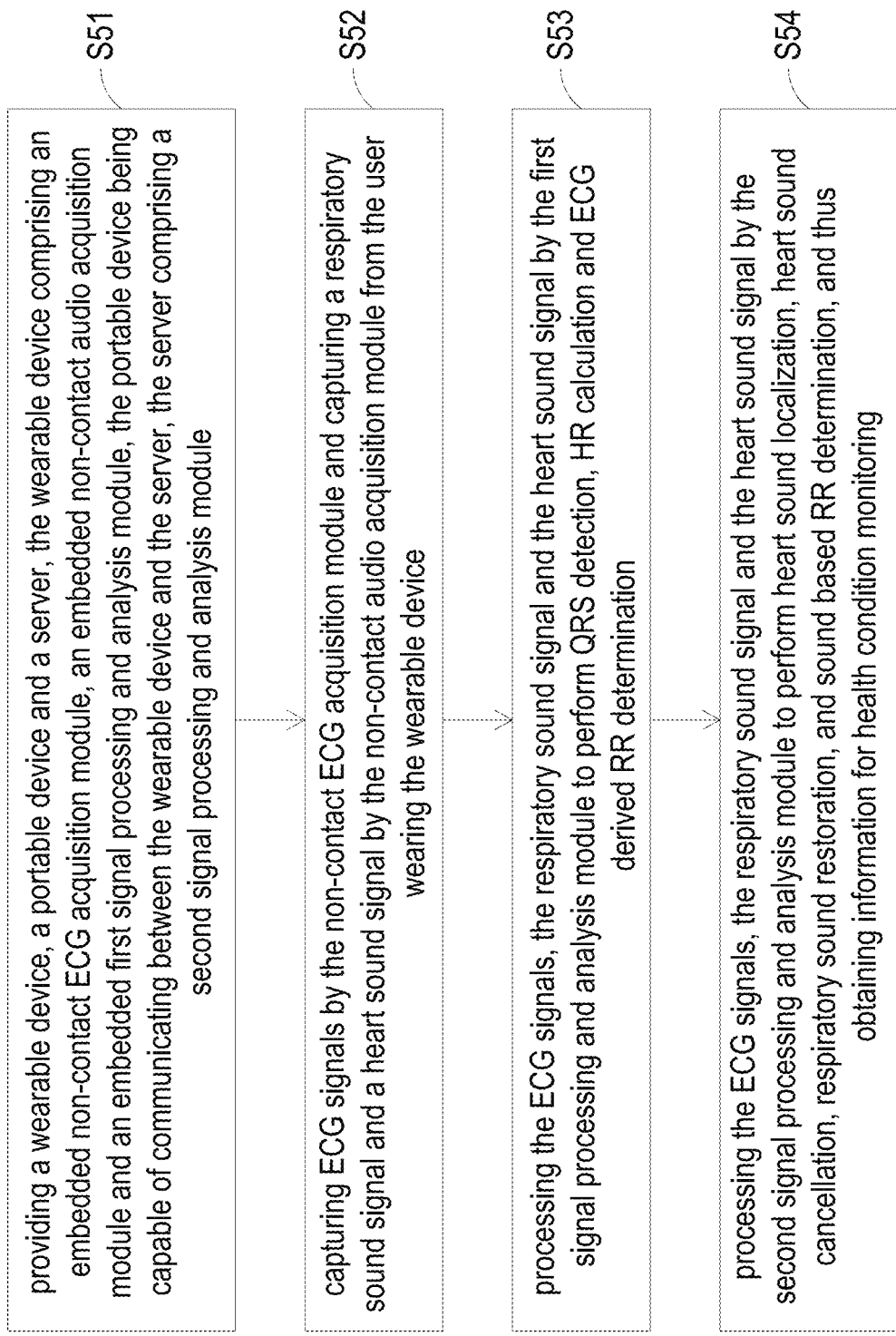

SYSTEM AND METHOD FOR HEALTH CONDITION MONITORING

CROSS-REFERENCE TO RELATED APPLICATION

This application claims priority to Singapore Patent Application No. 10201708876V, filed on Oct. 30, 2017. The entire content of the above-mentioned patent application is incorporated herein by reference for all purposes.

FIELD OF THE DISCLOSURE

The present invention relates to a system and a method for health condition monitoring, and more particularly to a system and a method for health condition monitoring suitable for long term use.

BACKGROUND OF THE DISCLOSURE

Nowadays, chronic heart problems and respiratory disorders are common progressive diseases, which are major causes of disabilities and leading causes of death. Monitoring and management of these diseases are important for medical care and can improve the quality of life for patients. In a wider circumstance, preventative monitoring allows health disorders to be detected during activities for military personnel while performance monitoring helps to improve the training via heart rate and breathing for sportsmen.

Frequent monitoring of heart and respiratory functions can provide crucial information but frequent visit to hospitals is costly and inconvenient. Thus, some electronic systems have been developed for health condition monitoring. However, these systems restrict the movement of the user and may require the user to be physically connected to stationary machines, which is inconvenient and uncomfortable for use or even long term use. In addition, these systems either only monitor single function for heart or lung or can detect both heart and lung activities only within short period of time.

Therefore, there is a need of providing a system and a method for health condition monitoring to obviate the drawbacks encountered from the prior arts.

SUMMARY OF THE DISCLOSURE

An object of the present invention is to provide a system and a method for health condition monitoring which can monitor both the heart and the lung functions of the user at anywhere and over a long duration with comfort.

In accordance with an aspect of the present invention, there is provided a system for health condition monitoring including a wearable device, a portable device and a server. The portable device is capable of communicating between the wearable device and the server. The system for health condition monitoring further includes a non-contact ECG (electrocardiography) acquisition module, a non-contact audio acquisition module, a first signal processing and analysis module and a second signal processing and analysis module. The non-contact ECG acquisition module is embedded in the wearable device for capturing ECG signals from a user wearing the wearable device. The non-contact audio acquisition module is embedded in the wearable device for capturing a respiratory sound signal and a heart sound signal from the user wearing the wearable device. The first signal processing and analysis module is embedded in the wearable device and connected with the non-contact ECG acquisition module and the non-contact audio acquisition module. The first signal processing and analysis module is used for receiving and processing the ECG signals, the respiratory sound signal and the heart sound signal from the non-contact ECG acquisition module and the non-contact audio acquisition module. Particularly, QRS detection, HR (heart rate) calculation and ECG derived RR (respiratory rate) determination are performed in the first signal processing and analysis module. The second signal processing and analysis module is provided on the server for receiving and processing the ECG signals, the respiratory sound signal and the heart sound signal uploaded by the portable device. Particularly, heart sound localization, heart sound cancellation, respiratory sound restoration, and sound based RR determination are performed in the second signal processing and analysis module, so as to obtain information for health condition monitoring.

In accordance with another aspect of the present invention, there is provided a method for health condition monitoring. The method includes steps of: (a) providing a wearable device, a portable device and a server, the wearable device comprising an embedded non-contact ECG acquisition module, an embedded non-contact audio acquisition module and an embedded first signal processing and analysis module, the portable device being capable of communicating between the wearable device and the server, the server comprising a second signal processing and analysis module; (b) capturing ECG signals by the non-contact ECG acquisition module and capturing a respiratory sound signal and a heart sound signal by the non-contact audio acquisition module from the user wearing the wearable device; (c) processing the ECG signals, the respiratory sound signal and the heart sound signal by the first signal processing and analysis module to perform QRS detection, HR (heart rate) calculation and ECG derived RR (respiratory rate) determination; and (d) processing the ECG signals, the respiratory sound signal and the heart sound signal by the second signal processing and analysis module to perform heart sound localization, heart sound cancellation, respiratory sound restoration, and sound based RR determination, and thus obtaining information for health condition monitoring.

BRIEF DESCRIPTION OF THE DRAWINGS

FIG. 14 is a flow chart illustrating a method for health condition monitoring according to an embodiment of the present invention.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
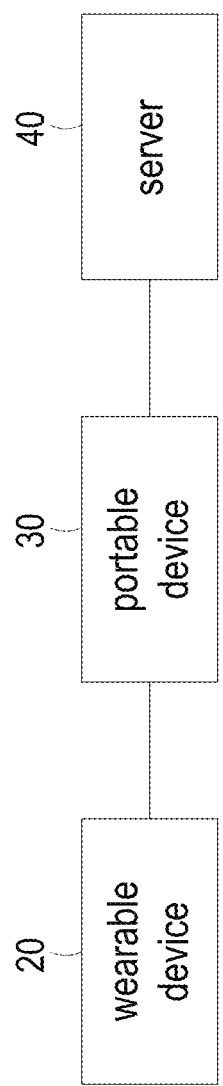
FIG. 1 is a diagram illustrating a system for health condition monitoring according to an embodiment of the present invention.

FIG. 1 is a diagram illustrating a system for health condition monitoring according to an embodiment of the present invention. As shown in FIG. 1, the system 1 for health condition monitoring includes a wearable device 20, a portable device 30 and a server 40. When the wearable device 20 is worn by a user, the ECG (electrocardiography), the heart sound and the respiratory sound of the user can be acquired. The wearable device 20 can communicate with the portable device 30 for data transmission. Moreover, the data can be further uploaded to the server 40 through the internet web services. By means of the portable device 30 and the server 40, the doctors, caretakers and family members of the user can retrieve data or be informed of situation where the user is in need of care or emergency medical treatments. Preferably but not exclusively, the wearable device 20 is a wearable vest and the portable device 30 is a smart phone or a tablet.

Figure 2:
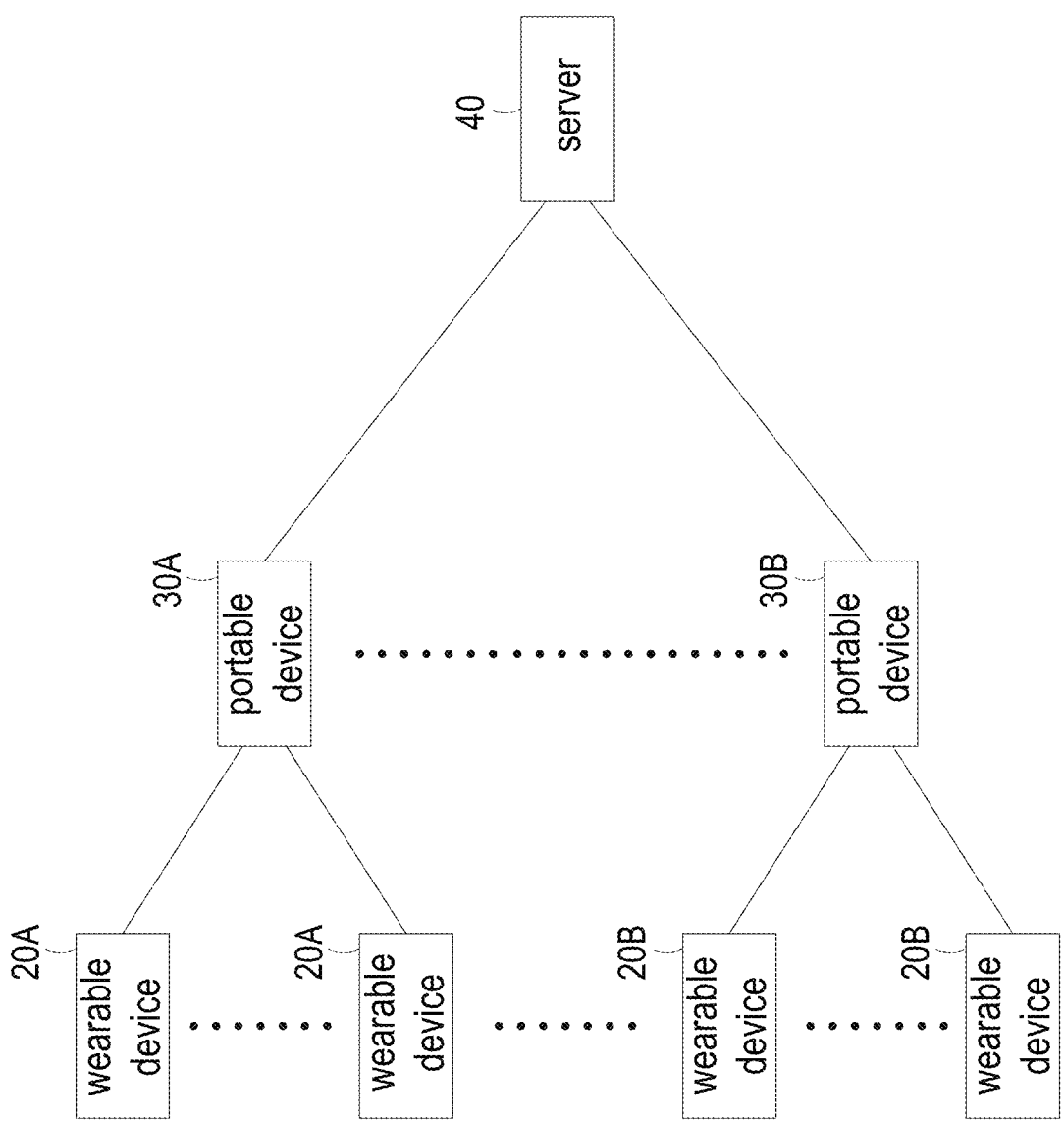
FIG. 2 is a diagram illustrating a system for health condition monitoring according to another embodiment of the present invention.

FIG. 2 is a diagram illustrating a system for health condition monitoring according to another embodiment of the present invention. As shown in FIG. 2, the system 1 may include plural wearable devices 20A, 20B and plural portable devices 30A, 30B. The plural wearable devices 20A may communicate with the same portable device 30A, and the plural wearable devices 20B may communicate with the same portable device 30B. For example, the plural wearable devices 20A may be worn by family members, so that the health conditions of the family may be monitored on the same portable device 30A. Similarly, the plural wearable devices 20B may be worn by members of another family, sport team or military unit, so as to monitor the health conditions of the members for the same group on the same portable device 30B.

Figure 3:
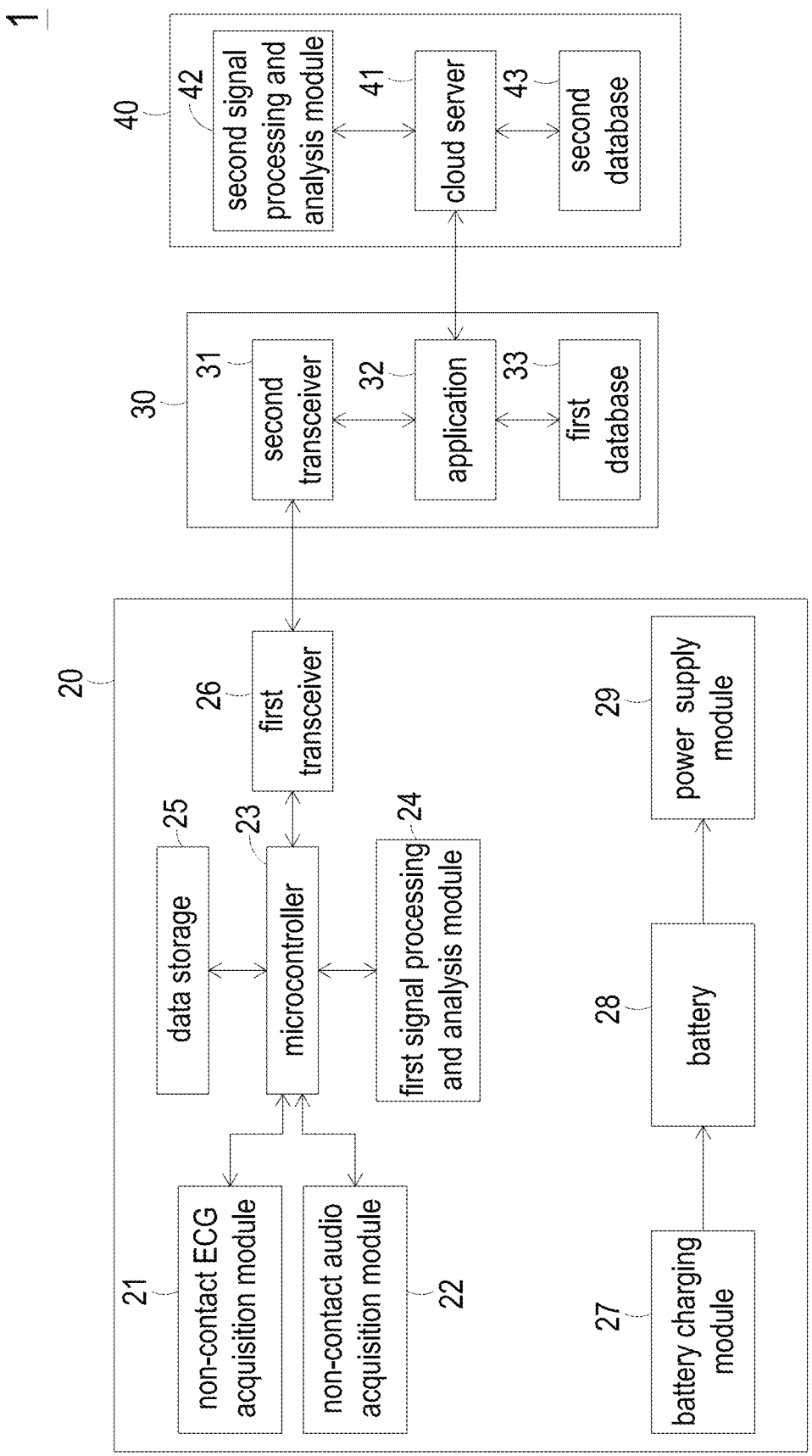
FIG. 3 is a detailed diagram illustrating the system for health condition monitoring of FIG. 1.

FIG. 3 is a detailed diagram illustrating the system for health condition monitoring of FIG. 1. As shown in FIG. 3, the wearable device 20 includes a non-contact ECG acquisition module 21 and a non-contact audio acquisition module 22 to acquire ECG signals and audio signals, respectively, from the user wearing the wearable device 20. The non-contact ECG acquisition module 21 and the non-contact audio acquisition module 22 are embedded in the wearable device 20 and do not directly contact the skin of the user. In other words, direct skin contact is not necessary for the system 1 for health condition monitoring of the present invention, so the user can be fully clothed. This not only fulfils the requirement of hygiene purpose but also makes the wearer feel comfortable to improve the compliance of long term use.

Figure 4:
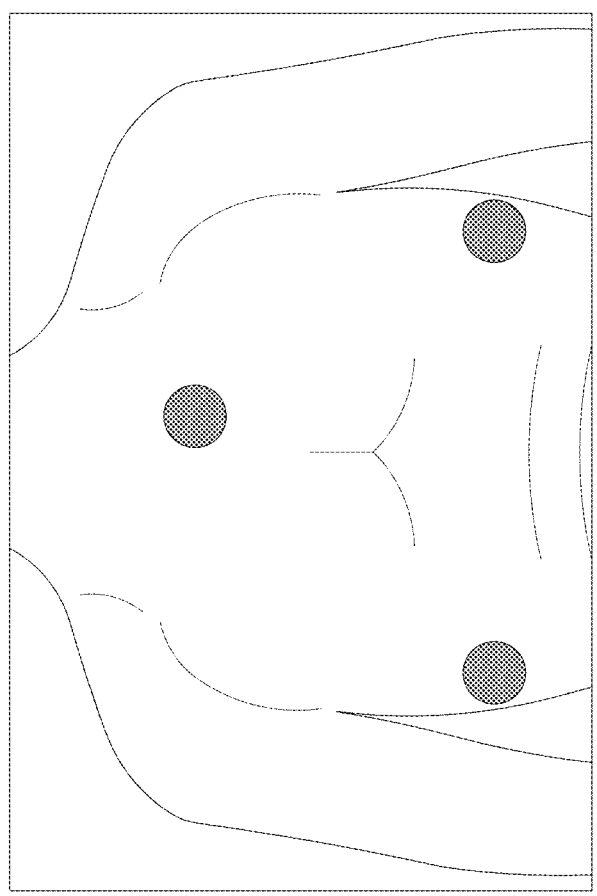
FIG. 4 is a diagram illustrating the positions of the three non-contact ECG sensors on a human body while wearing the wearable device.

In an embodiment, the non-contact ECG acquisition module 21 includes three or more non-contact ECG sensors. FIG. 4 is a diagram illustrating the positions of the three non-contact ECG sensors on a human body while wearing the wearable device. When the user is wearing the wearable device 20, the three non-contact ECG sensors will be placed at the positions shown as grey circles in FIG. 4, which are at the top of the manubrium, the left side of the ninth rib, and the right side of the ninth rib. The ECG signals captured from the non-contact ECG sensors located at the top of the manubrium vs. the left side of the ninth rib have similar waveform as the traditional ECG. In addition, since there are relatively less muscles at both sides of the ninth rib, the ECG signals captured from the non-contact ECG sensors located at the left side of the ninth rib vs. the right side of the ninth rib are interfered less by muscle movement, and are thus chosen for ECG signal records during exercises.

Figure 5:
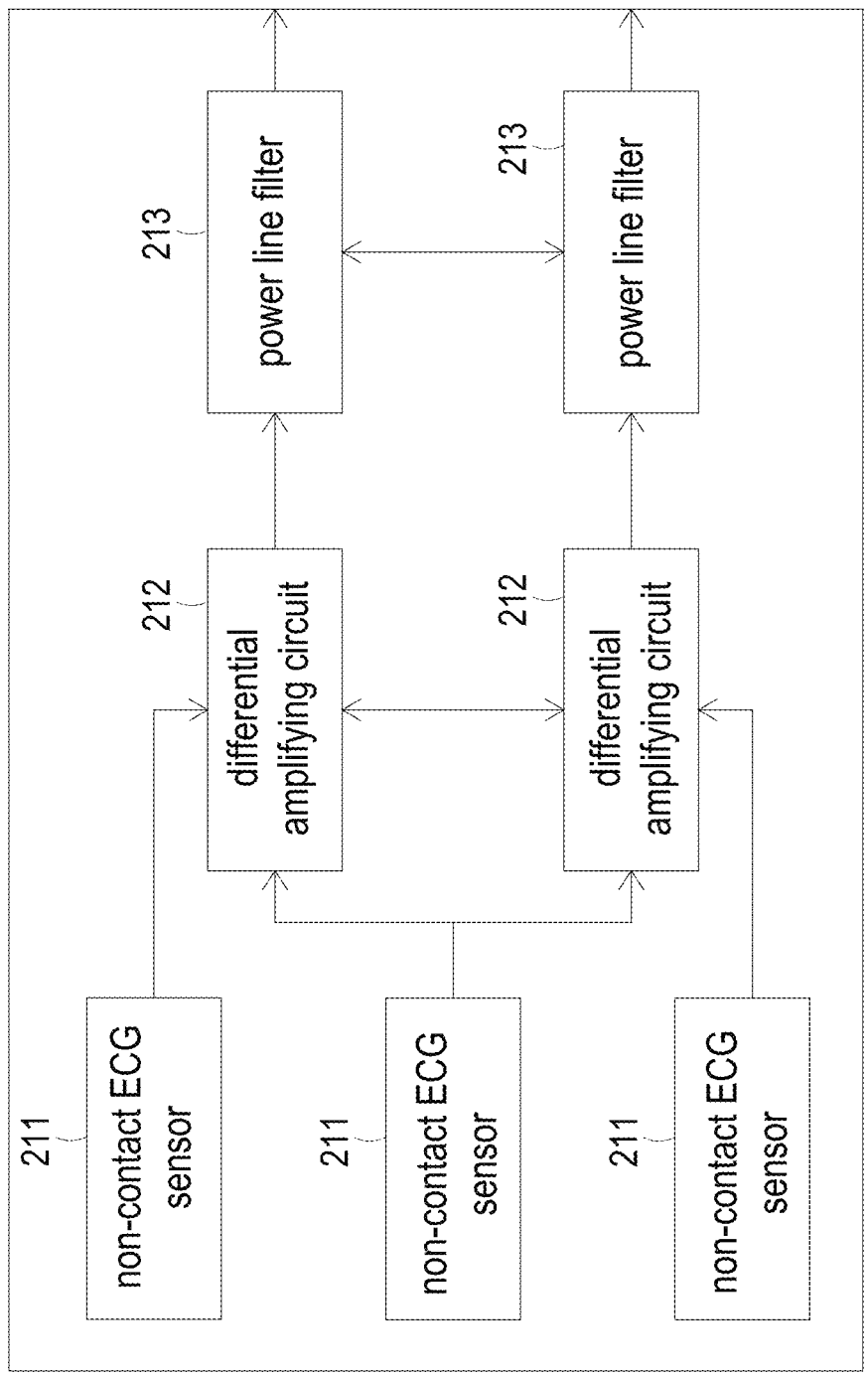
FIG. 5 is a circuit diagram illustrating the non-contact ECG acquisition module according to an embodiment of the present invention.

The non-contact ECG acquisition module 21 is used for capturing ECG signals from the user wearing the wearable device 20 through the non-contact ECG sensors. FIG. 5 is a circuit diagram illustrating the non-contact ECG acquisition module according to an embodiment of the present invention. As shown in FIG. 5, the non-contact ECG acquisition module 21 includes three non-contact ECG sensors 211 based on capacitance, two differential amplifying circuits 212 and two power line filters 213. The three non-contact ECG sensors 211 capture the ECG signals, and then the ECG signals are pre-processed by the non-contact ECG acquisition module 21. A pair of non-contact ECG sensors 211 will provide one differential ECG signal. In an embodiment, the ECG signals from paired non-contact ECG sensors 211, i.e. sensors located at the top of the manubrium vs. the left side of the ninth rib and sensors located at the left side of the ninth rib vs. the right side of the ninth rib, are differentiated by the differential amplifying circuit 212 and then filtered by the power line filter 213. Accordingly, two sets of differential ECG signals are acquired from the three non-contact ECG sensors 211 in the wearable device 20. One set of differential non-contact ECG signal provides an ECG signal that emulates 3-leads ECG while another set of differential non-contact ECG signal provides an ECG signal that is robust to motions of user's daily activities. The emulated 3-leads ECG allows medical practitioners to examine user's ECG signal they are familiar with while the robust ECG signals are used for IBI (inter-beat interval) computation.

Therefore, by means of the three non-contact ECG sensors 211 and the dual differential amplifying circuits 212, the non-contact ECG acquisition module 21 is configured to emulate conventional 3-leads ECG output, and is resistant to motions of user and suitable for long term signal acquisition.

Figure 6:
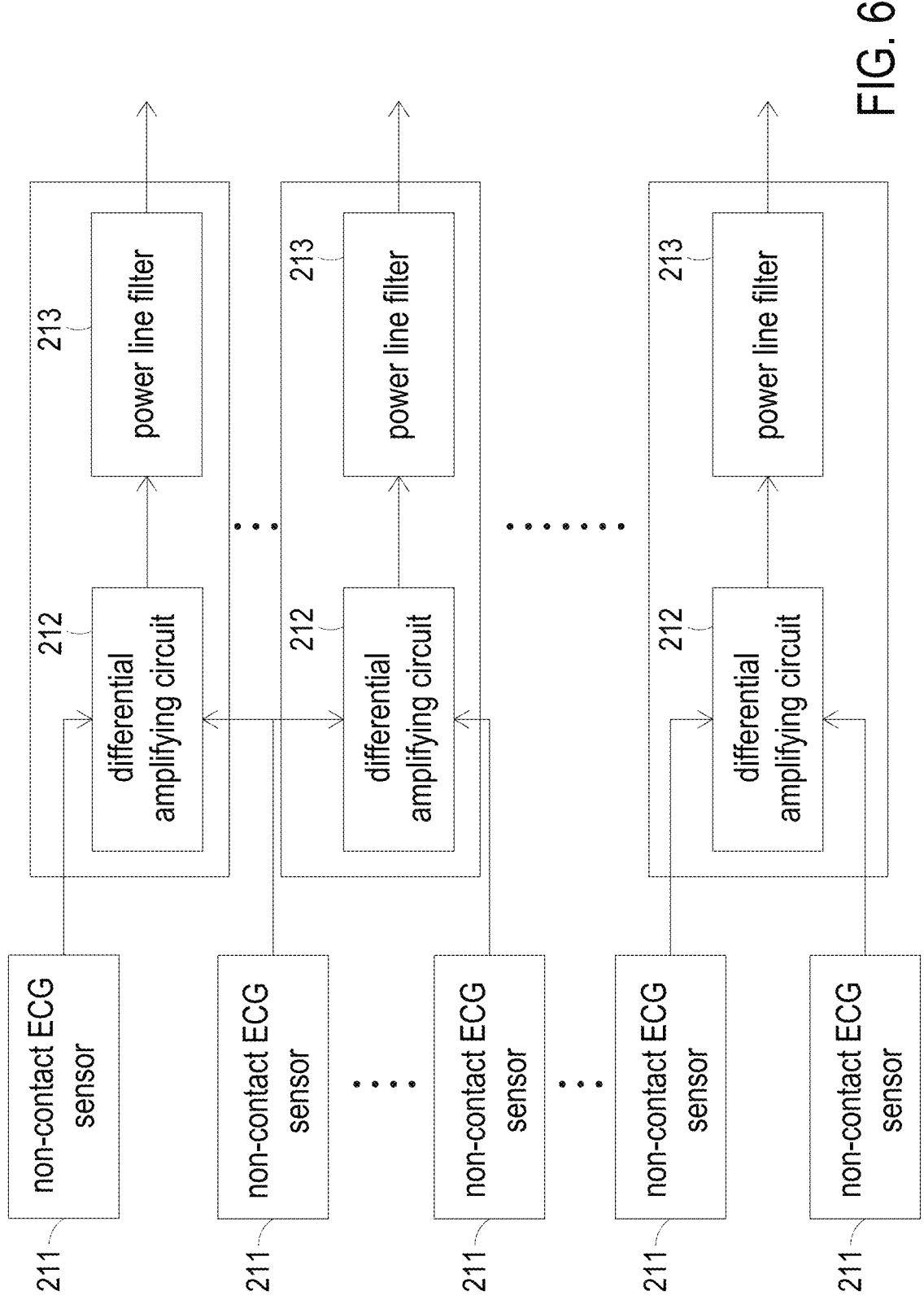
FIG. 6 is a circuit diagram illustrating the non-contact ECG acquisition module according to another embodiment of the present invention.

Nevertheless, the numbers of the non-contact ECG sensors 211, the differential amplifying circuits 212 and the power line filters 213 included in the non-contact ECG acquisition module 21 are not limited to those shown in FIG. 5. FIG. 6 is a circuit diagram illustrating the non-contact ECG acquisition module according to another embodiment of the present invention. As shown in FIG. 6, the non-contact ECG acquisition module 21 includes more than three non-contact ECG sensors 211, more than two differential amplifying circuits 212 and more than two power line filters 213. The non-contact ECG sensors 211 capture the ECG signals, and then the ECG signals are pre-processed by the non-contact ECG acquisition module 21. Similar to the embodiment shown in FIG. 5, a pair of non-contact ECG sensors can provide one differential ECG signal, which is further filtered by the power line filter 213.

In an embodiment, the ECG signal pre-processing further includes ground equalization, isolated gain, and other differential subsystems. All parameters for the ECG signal pre-processing are tunable from a microcontroller 23 of the wearable device 20, and this allows tuning of circuitries for different users.

Figure 7:
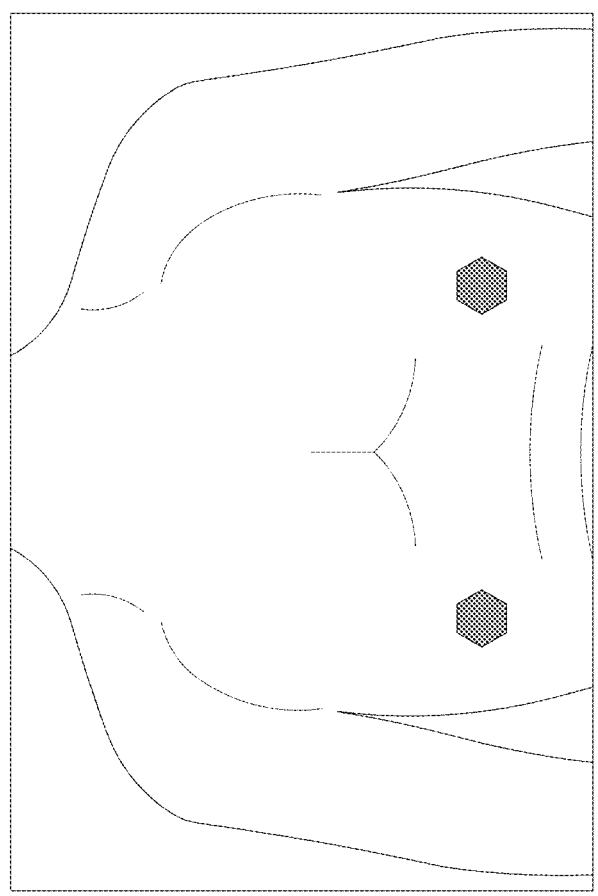
FIG. 7 is a diagram illustrating the positions of the two non-contact audio sensors on a human body while wearing the wearable device.

In an embodiment, the non-contact audio acquisition module 22 includes two or more non-contact audio sensors for capturing a respiratory sound signal and a heart sound signal from the user wearing the wearable device 20. FIG. 7 is a diagram illustrating the positions of the two non-contact audio sensors on a human body while wearing the wearable device. When the user is wearing the wearable device 20, the two non-contact audio sensors will be placed at the positions shown as grey hexagons in FIG. 7. The primary non-contact audio sensor is located at the lung area in the right chest, and the auxiliary non-contact audio sensor is located at the heart area in the left chest, so as to capture the respiratory sound signal by the primary audio path and capture the heart sound signal by the secondary audio path, respectively. In an embodiment, the non-contact audio sensor is a MEMS (microelectro-mechanical system) microphone sensor.

Figure 8:
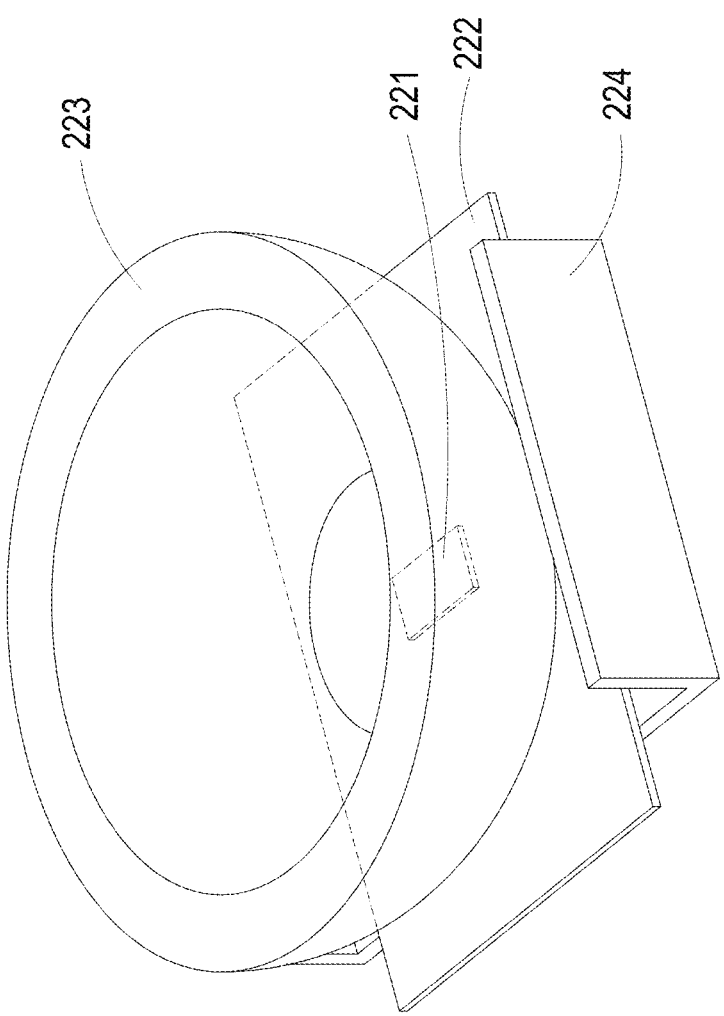
FIG. 8 is a schematic view illustrating the non-contact audio sensor.

FIG. 8 is a schematic view illustrating the non-contact audio sensor. As shown in FIG. 8, the non-contact audio sensor includes an audio sensor chip 221, a flexible PCB board 222, an acoustic chamber 223 and a holder 224. The audio sensor chip 221 is mounted on the flexible PCB board 222, and the flexible PCB board 222 is assembled with the acoustic chamber 223 by the holder 224 to form an integrated component. The bell-shaped acoustic chamber 223 totally encloses the audio sensor chip 221 and uses bell-shaped waveguide to optimize transfer of sound from user's body to the audio sensor chip 221 while blocking external soundwave, so as to amplify lung or heart sound and attenuate external undesirable sound.

Referring to FIG. 3 again. The wearable device 20 also includes a microcontroller 23, a first signal processing and analysis module 24, a data storage 25 and a first transceiver 26, which are all embedded in the wearable device 20. The microcontroller 23 is connected with the non-contact ECG acquisition module 21 and the non-contact audio acquisition module 22, and transmits the ECG signals and the audio signals from the non-contact ECG acquisition module 21 and the non-contact audio acquisition module 22 to the first signal processing and analysis module 24 for further processing. In an embodiment, the first signal processing and analysis module 24 includes a digital signal processor. The captured signals and processed data can be stored in the data storage 25. In an embodiment, the data storage 25 is a flash memory. The microcontroller 23 manages the operations of the non-contact ECG acquisition module 21, the non-contact audio acquisition module 22, and the first signal processing and analysis module 24. The microcontroller 23 also manages the operations of the data storage 25, and manages the communication with the portable device 30 through the first transceiver 26. Preferably but not exclusively, the microcontroller 23 is a Bluetooth microcontroller, and the first transceiver 26 is a Bluetooth transceiver.

The wearable device 20 further includes a battery charging module 27, a battery 28 and a power supply module 29. The wearable device 20 is powered by the battery 28. In an embodiment, the battery 28 is a lithium polymer battery but not limited thereto. The battery charging module 27 is connected with the battery 28 and manages the charging procedure of the battery 28. The power supply module 29 is connected with the battery 28 and converts the power from the battery 28 into the required voltages for the non-contact ECG acquisition module 21, the non-contact audio acquisition module 22, the microcontroller 23, the first signal processing and analysis module 24, the data storage 25 and the first transceiver 26.

Figure 9:
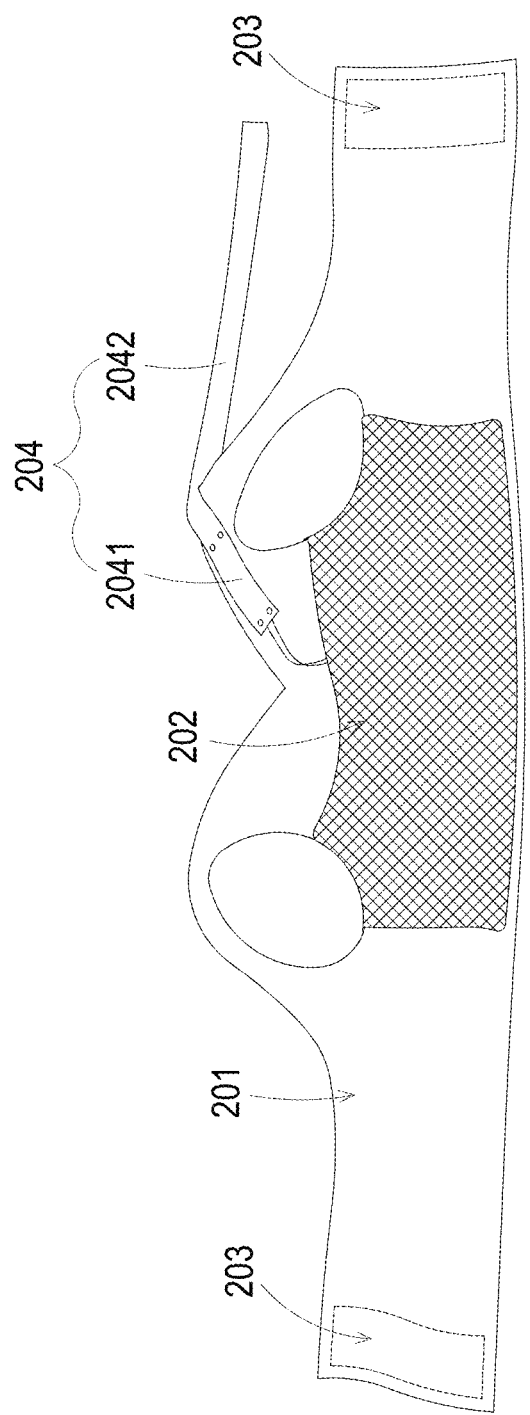
FIG. 9 is a schematic view illustrating the wearable device.
Figure 10:
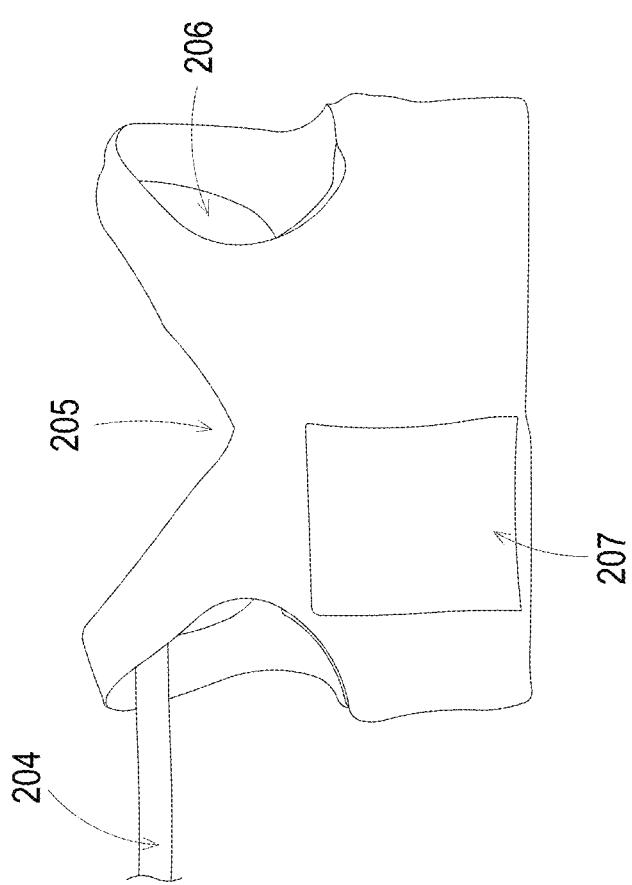
FIG. 10 is another schematic view illustrating the wearable device in wearing state.

FIG. 9 is a schematic view illustrating the wearable device, and FIG. 10 is another schematic view illustrating the wearable device in wearing state. As shown in FIGS. 9 and 10, the wearable device 20 is a wearable vest, which is used to host the non-contact ECG acquisition module 21 and the non-contact audio acquisition module 22 and to make sure the wearer comfortable. The wearable device 20 is with two-layer design which is fully detachable. The wearable device 20 includes an outer layer 201 and an inner layer 202. The outer layer 201 is made of elastic fabric and hence it is stretchable and can apply pressure to the body of the wearer. The inner layer 202 is made of meshed clothing with 100% cotton which is comfortable for users to wear. The non-contact ECG acquisition module 21 and the non-contact audio acquisition module 22 and wires thereof are attached to the inner layer 202 and deployed between the outer layer 201 and the inner layer 202. The outer layer 201 and the inner layer 202 are bonded together using snap fasteners, so the wearable device 20 is washable to fulfill the requirement for hygiene purpose. Most important, the design of the wearable device 20 makes the non-contact ECG acquisition module 21 and the non-contact audio acquisition module 22 fastened firmly to the proper positions to obtain signals with good quality. Accordingly, the wearable device 20 is able to provide safety, capability, convenience and comfort to the users.

In an embodiment, all sensors of the non-contact ECG acquisition module 21 and the non-contact audio acquisition module 22 are built as flexible PCB to make the wearable device 20 comfortable for the user to wear. To secure the ECG sensors of the non-contact ECG acquisition module 21 and the audio sensors of the non-contact audio acquisition module 22 to the proper positions of the human body, each of the sensors is independently attached to a patch, and the sensor patches are sewed to the proper positions in the inner-side of the inner layer 202 to hold the sensors. Therefore, the non-contact ECG acquisition module 21 and the non-contact audio acquisition module 22 are deployed between the outer layer 201 and the inner layer 202, and the sensors of the modules 21 and 22 are fastened firmly to the proper positions and face the human body to obtain signals with good quality.

In an embodiment, an inner conduit is provided to contain wires of the non-contact ECG acquisition module 21 and the non-contact audio acquisition module 22 therein so the wires are invisible to the user. The inner conduit is also sewed to the inner-side of the inner layer 202 and deployed between the outer layer 201 and the inner layer 202. In addition, rubber pads are provided under the sensor patches of the non-contact ECG acquisition module 21 to make the ECG sensors more protruding so that the wearable device 20 needs not to be too tight.

In an embodiment, the wearable device 20 includes two bonding parts 203 located at two open sides of the wearable device 20, which makes the wearable device 20 convenient to put on. Preferably but not exclusively, the two bonding parts 203 are hook-and-loop fasteners, such as Vecro. It is flexible for the user with different sizes by adjusting the bonding position of two bonding parts 203.

In an embodiment, the wearable device 20 uses conductive clothing adopted for soft grounding. The wearable device 20 includes a two-section strip 204 made of conductive clothing to ensure secure grounding. The two-section strip 204 includes a first portion 2041 and a second portion 2042. The first portion 2041 is connected with the electronic components in the wearable device 20, such as the non-contact ECG acquisition module 21 and the non-contact audio acquisition module 22. The second portion 2042 is connected with the first portion 2041, and is replaceable to replace the worn-out portion.

As shown in FIG. 10, a deep-V collar 205 is provided around the neck of the wearer, and two large indentations 206 are provided around the shoulders and arms of the wearer, which are designed to leave more space to the wearer to make him feel comfortable. Besides, the large indentations 206 make the wearable device 20 less movable while the wearer moving his arms. Therefore, the ECG signals can be obtained with high quality because of reduced interference.

In an embodiment, the wearable device 20 further includes a pocket 207 disposed on the outside of the wearable device 20. The pocket 207 is used to accommodate hard components of the system, such as the battery 28, so that wearable device 20 is comfortable for the user to wear.

Referring to FIG. 3 again. The portable device 30 includes a second transceiver 31, an application (App) 32 and a first database 33. The second transceiver 31 of the portable device 30 is communicated with the first transceiver 26. Preferably but not exclusively, the second transceiver 31 is also a Bluetooth transceiver, and the communication between the first transceiver 26 and the second transceiver 31 is through the Bluetooth protocol catered for low power consumption. NFC (Near Field Communication) system is used to power up the wearable device 20 from deep sleep and pairing for Bluetooth, which removes the need for mechanical switches and button for wearable device 20. The App 32 is designed to communicate with the wearable device 20 for its operation and data transmission, and also communicate with the server 40 for its operation and data transmission. The data can be stored in the first database 33 and can be observed on the portable device 30 for result display or further uploaded to the server 40 through internet web services, such as mobile data network.

Except for data transmission, the portable device 30 provides various functionalities. By the customized App 32, the portable device 30 is able to provide system control, result display and cloud services. For example, the portable device 30 can display the real-time waveforms of the signals for real-time monitoring. The user may listen to the lungs/heart sounds through the portable device 30. The user can control the system 1 via the portable device 30. Moreover, the portable device 30 can display or issue the warning/alarm signal when the user is in need of care or emergency medical treatments.

The server 40 includes a cloud server 41, a second signal processing and analysis module 42 and a second database 43. The cloud server 41 is interacted with the application 32 of the portable device 30 through the internet web services to receive the data transmitted from the portable device 30 by the application 32. The received data, including the ECG signals and the audio signals, can be further processed by the second signal processing and analysis module 42. The received data and the processed data can be stored in the second database 43.

Figure 11:
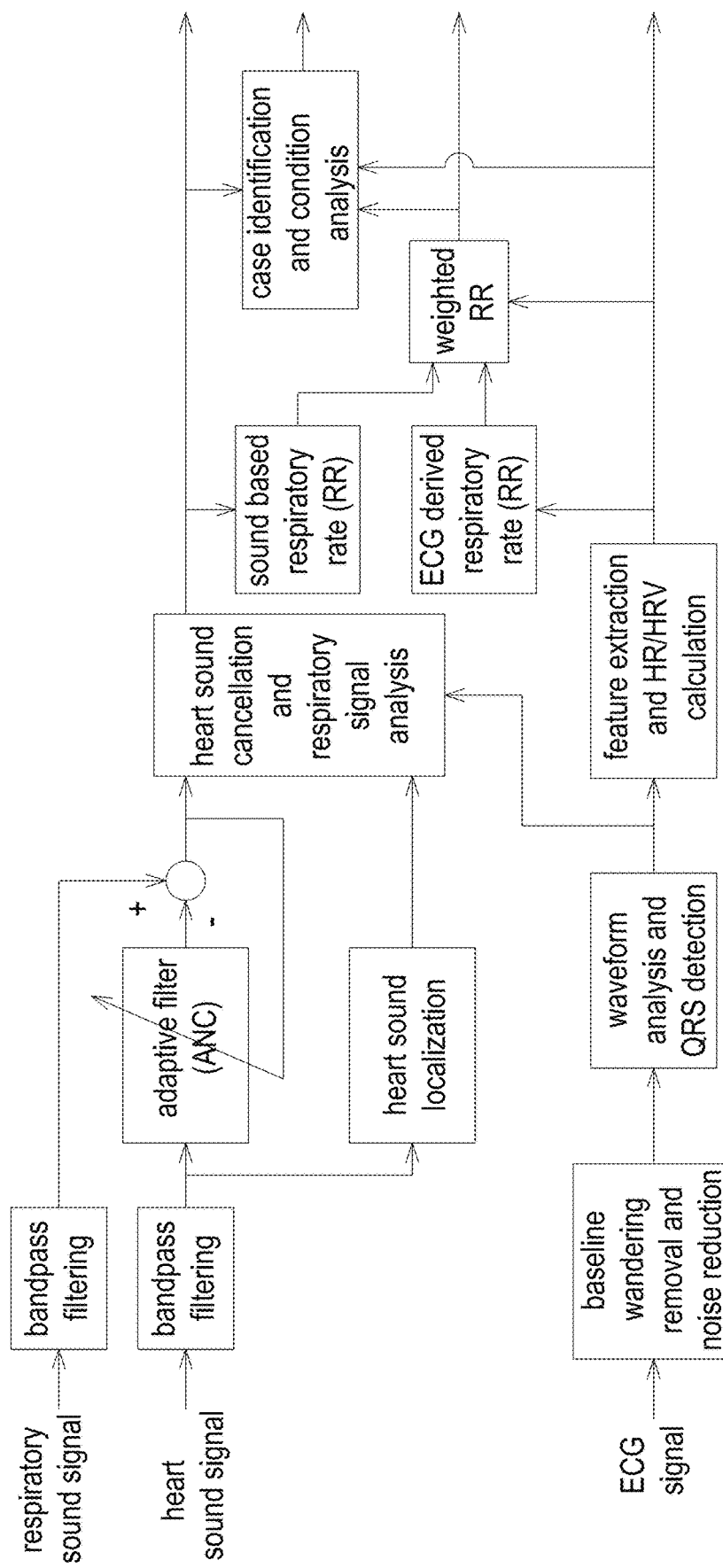
FIG. 11 is a diagram illustrating a method for health condition monitoring according to an embodiment of the present invention.

FIG. 11 is a diagram illustrating a method for health condition monitoring according to an embodiment of the present invention. For ECG signal processing, the ECG signal obtained by the non-contact ECG acquisition module 21 is first filtered to remove the baseline wandering and other noise out of the desired band. The filtering can be realized by different techniques according to the application scenario, and can be performed in both the first signal processing and analysis module 24 of the wearable device 20 and the second signal processing and analysis module 42 of the server 40. For example, when the filtering is performed in the second signal processing and analysis module 42 of the server 40, the filtering can be implemented by some sophisticated technique such as non-linear filtering to retain the details in the waveform of the signal. When the filtering is performed in the first signal processing and analysis module 24 of the wearable device 20, the filtering can be implemented by some simple technique such as linear filtering. However, other than the bandwidth usually used in filtering the ECG signal obtained by traditional ECG devices, the bandwidth used in the present invention depends on the characteristics of the ECG signal obtained by the non-contact ECG acquisition module 21. In an embodiment, the bandwidth used in filtering the ECG signal obtained by the non-contact ECG acquisition module 21 applied to the side of the user's body is 0.67-150 Hz. Particularly, the bandwidth 10-50 Hz is used in filtering the ECG signal to acquire a reliable QRS detection.

After the filtering for baseline wandering removal and noise reduction, waveform analysis and peak detection are conducted to the filtered ECG signal. Different techniques can be used to do this. For example, a derivative processing based technique can be used in the first signal processing and analysis module 24 of the wearable device 20 to detect the QRS complex, while in the second signal processing and analysis module 42 of the server 40, a template matching based technique can be applied to do this job.

Figure 12:
FIG. 12 is a diagram illustrating the QRS detection in the wearable device.

FIG. 12 is a diagram illustrating the QRS detection in the wearable device which uses a derivative processing based technique. The filtered ECG signal is differentiated to provide the QRS complex slope information. After the derivative processing, the signal is squared point by point to attenuate the noise and emphasize the ECG components (i.e. the ECG frequencies). Then the moving-window integration is applied to obtain the waveform feature information of the R wave. The QRS complex corresponds to the rising edge of the integration waveform. A fiducial mark for the temporal location of the QRS complex can be determined from this rising edge. Finally the threshold will be adjusted automatically to float over the noisy/interference components.

Figure 13:
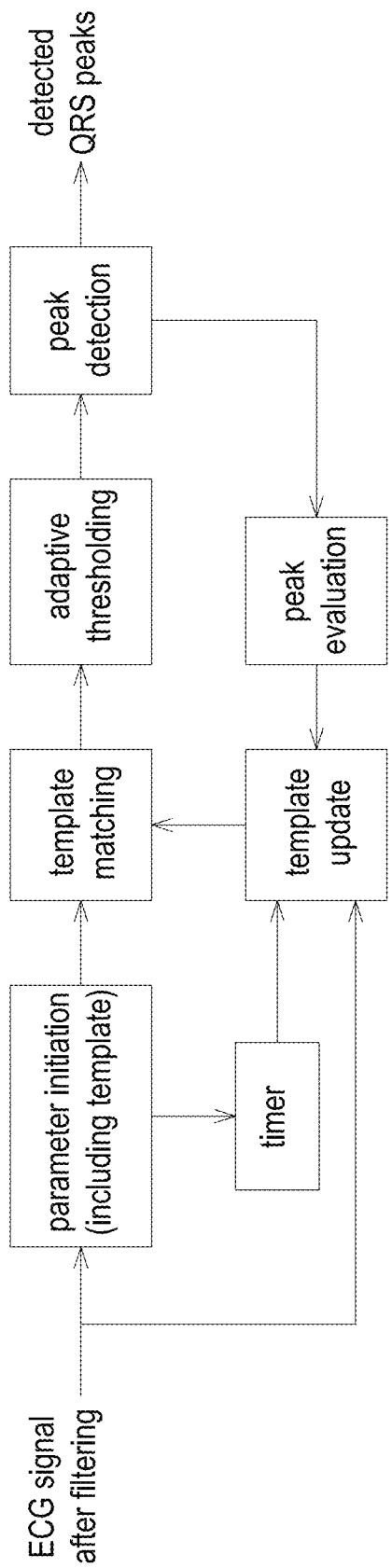
FIG. 13 is a diagram illustrating the QRS detection in the server.

FIG. 13 is a diagram illustrating the QRS detection in the server which uses a template matching based technique. For the template matching based technique, the template pre-stored in the system will be used during the initial phase. The template matching is conducted by correlating the template model with the filtered ECG signal. Adaptive thresholding is then applied to detect the R peaks. The detected peaks will be evaluated, and IBI (inter-beat interval) will be calculated. Those intervals which exceed the pre-defined percentage (e.g. 120%) of their previous intervals will be treated as unreliable and the corresponding peaks will be discarded. For those peaks which pass the evaluation, the corresponding QRS complex will be used to update the template. The template will be updated regularly once the timer reaches the pre-defined value of time duration (e.g. 10 seconds).

Afterward, the output of the waveform analysis and QRS detection will be used to do the feature extraction and heart rate (HR) and heart rate variability (HRV) calculation, as shown in FIG. 11. The results of the feature extraction and HR/HRV calculation are not only a part of the final output but also intermediate output that would be exploited in further processing steps.

For audio signal processing, the respiratory sound signal and the heart sound signal captured by the two non-contact audio sensors of the non-contact audio acquisition module 22 are first processed in the first signal processing and analysis module 24 of the wearable device 20 for bandpass filtering and adaptive noise cancellation (ANC). In an embodiment, the first signal processing and analysis module 24 includes an adaptive filter with ANC configuration. As shown in FIG. 9, the respiratory sound signal and the heart sound signal are first filtered to compress the components out of the desired band. Then the adaptive filter with ANC configuration is applied to suppress both the ambient noise and the heart sound simultaneously.

In other words, the system 1 for health condition monitoring uses a dual-channel framework consisting of two audio sensors. The heart sound signal captured by the auxiliary non-contact audio sensor and the respiratory sound signal captured by primary non-contact audio sensor constitute the configuration of ANC, where both the ambient noise and the heart sound will be suppressed.

The heart sound signal captured by the auxiliary non-contact audio sensor is not only used as a part of the ANC configuration to suppress the heart sound, but also used to estimate the locations of heart sound portions with an algorithm proposed in the present invention, which is named multiband products based on FFT (fast Fourier transform) coefficients. The short-time Fourier transform (STFT) is applied to the filtered heart sound signal from the auxiliary non-contact audio sensor every particular time period to transform it into frequency domain. Setting the time period to a pre-defined value $N_1$, where $N_1$ ranges from 10 ms to 1000 ms. In an embodiment, $N_1$ ranges from 32 ms to 64 ms. The number of selected samples in every frame for one STFT is $R_s * N_1 = N_{fft}$, where $R_s$ is the sampling rate. The overlap between the successive frames could be 0-100%. In an embodiment, the overlap between the successive frames is 20-80%, more preferably 40-60%, and most preferably 50%. The two-dimension representation of the filtered signal along the time and frequency axis is given by the STFT as the following formula:

$$S(\tau, f) = \int_{-\infty}^{+\infty} s(t) h^*(t-\tau) e^{-j2\pi ft} dt \quad (1)$$

where s(t) is the time-domain signal, h(t−τ) is the window function, τ is the shift in time, and "*" represents the complex conjugate. Once the FFT coefficients S(τ, f) are obtained, the multiband products can be calculated by multiplying the FFT coefficients of the desired sub-bands as the following formula:

$$P_{j,k}(\tau) = \prod_{i=j}^{k} |S(\tau, i)| \quad (2)$$

where j is a positive number equal to or greater than 0 which corresponds to the lower bound of the desired sub-band of the heart sound, k is a positive number greater than or equal to j and corresponds to the upper bound of the desired sub-band of the heart sound, $P_{j,k}$ is the multiband product of FFT coefficients from the jth sub-band to the kth sub-band, and S(τ, i) is the FFT coefficient. The multiband product $P_{j,k}$ is compared with an adaptive threshold. If the multiband product $P_{j,k}$ is greater than the adaptive threshold, the corresponding 2 is identified as belonging to the heart sound portion.

The accuracy of estimation of heart sound locations can be improved by combining the information provided by ECG signals and the locations estimated from the audio signals. There is a relationship between the ECG signal and the heart sound signal, pre-ejection period (PEP), which is the time interval from R-peak of ECG to the first heart sound (S1) of PCG (phonocardiogram) recorded from the chest. Since ECG signal and the respiratory sound signal are collected at the same time and the approximate value of PEP is around 100 ms, when the R-peak is detected, the processed respiratory sound signal can be searched at the portion about 100 ms apart from the point of the R-peak. Therefore S1 can be identified with higher accuracy. The information of accurate locations of heart sounds is then exploited in the further step to remove the residual heart sound from the output of the ANC for heart sound cancellation.

The restoration of respiratory sound during the removed heart sound portions can be done by estimating the removed data by linear prediction, using either autoregressive (AR) or moving average (MA) models. The STFT is applied to the signal at the output of ANC similar as described above, therefore FFT coefficients $S_{ANC}(\tau, f)$ are obtained. Once the heart sound portions are localized, the information is used in the ANC path, i.e. the FFT coefficients in $S_{ANC}(\tau, f)$ corresponding to the heart sound portions will be removed from $S_{ANC}(\tau, f)$. The gap between two successive respiratory sound portions is filled in by interpolated FFT coefficients obtained from the linear prediction. The linear prediction is conducted in each sub-band of the desired frequency bands, using either AR or MA models. The refurbished FFT coefficients after interpolation are denoted as $S_{ANC,r}(\tau, f)$. Then IFFT (inverse FFT) is applied to the refurbished FFT coefficients to restore the respiratory sound. Therefore a cleaner respiratory signal can be used for respiration analysis.

Respiratory rate (RR) can be estimated from ECG signals. After the R-peak detection is done, IBI can be calculated from the locations of R-peaks. Applying spectrum analysis to the IBI, the respiratory rate can be estimated by searching the maximum point in the frequency range of 0.2-1 Hz of the spectrum. Accordingly, the ECG derived RR is obtained.

Alternatively, the respiratory rate can also be estimated from the cleaned respiratory signals after heart sound cancellation by a spectral processing method. A quadratic detection function is applied to the FFT coefficients to obtain the spectral parameters. This operation can be performed as follows by multiplying the squared frequency with the power of its FFT coefficients as the following formulas:

$$Q(\tau, f_n) = |S_{ANC,r}(\tau, f_n)|^2 \cdot f_n^2 \quad (n = n_1, n_1 + 1, \ldots n_2) \quad (3)$$

$$P(\tau) = \sum_{n=n_1}^{n_2} Q(\tau, f_n) \quad (4)$$

where τ is the shift in time, f is the frequency, $n_1$ is a positive number equal to or greater than 0 which corresponds to the lower bound of the desired sub-band of the respiratory sound, $n_2$ is a positive number greater than or equal to $n_1$ and corresponds to the upper bound of the desired sub-band of the respiratory sound, and $S_{ANC,r}(\tau, f)$ is the refurbished FFT coefficient. Then autocorrelation function is applied to this result and generally the second peak in the autocorrelation result represents the RR. Accordingly, the sound based RR is obtained. However in the case when one respiratory phase is more prominent, the RR may be better estimated by the first peak.

After the RR estimate is derived from the ECG signal and from the audio signals respectively, the sound based RR and the ECG derived RR are then combined by a weighted method to give the final result of RR. A score system is developed as the following formula to determine how to combine the individual estimates:

$$RR = w_{ecg} \cdot RR_{ecg} + w_{sound} \cdot RR_{sound} \quad (5)$$

where $0 \leq w_{ecg} \leq 1$, $0 \leq w_{sound} \leq 1$, $w_{ecg} + w_{sound} = 1$.

This method includes a logical analysis to choose the weights used in the RR combination, i.e. the weight will be assigned based on the quality of the signal itself. The signal with better quality will be assigned a heavier weight. The evaluation of signal quality will be approximated by the peak evaluation mentioned in the ECG signal processing. Before calculating the HRV, the RR-interval is corrected to get the NN-interval. The difference between the NN-interval and the RR-interval, i.e. the percentage on the number of RR-intervals that have been rectified, can be used as an indicator of the quality of the ECG signal. The values of weight pairs can be determined based on the indicator by looking up the table pre-defined in the system.

At last the features extracted from respiratory signal together with the features extracted from ECG signal, and the features induced from both the respiratory and ECG signals will be combined by data fusion analysis to give the final results on case identification and condition analysis of the wearer.

The data fusion may be used in different levels and aspects. The data fusion may be used in localizing heart sound portions from respiratory sound by combining position information derived from the secondary audio path and that from ECG signal. The data fusion may be used in calculation of RR by combining RR estimate derived from ECG signal and RR estimate derived from respiratory sound. The data fusion may be used in weighted RR combination by a score system based on logical analysis, i.e. RR estimate from better signal quality is assigned a heavier weight while signal quality is evaluated by the percentage of the number of RR intervals to be corrected to get NN-interval in ECG The data fusion may also be used in identification of specific events and health condition analysis by combing all information derived from the whole feature space, which is spanned by the individual spaces from ECG and respiration respectively.

The present invention also provides a method for health condition monitoring. FIG. 14 is a flow chart illustrating a method for health condition monitoring according to an embodiment of the present invention.

Firstly, a wearable device, a portable device and a server are provided (Step S51). The wearable device includes an embedded non-contact ECG acquisition module, an embedded non-contact audio acquisition module and an embedded first signal processing and analysis module. The portable device is capable of communicating between the wearable device and the server. The server includes a second signal processing and analysis module.

Then, ECG signals are captured by the non-contact ECG acquisition module, and a respiratory sound signal and a heart sound signal are captured by the non-contact audio acquisition module from the user wearing the wearable device (Step S52).

Subsequently, the ECG signals, the respiratory sound signal and the heart sound signal are processed by the first signal processing and analysis module to perform QRS detection, HR calculation and ECG derived RR determination (Step S53).

Afterward, the ECG signals, the respiratory sound signal and the heart sound signal are processed by the second signal processing and analysis module to perform heart sound localization, heart sound cancellation, respiratory sound restoration, and sound based RR determination, and thus obtaining information for health condition monitoring (Step S54).

Further, a final result of RR from the ECG derived RR and the sound based RR is obtained by a weighted method, where the RR from better signal quality is assigned a heavier weight.

The detailed signal processing and analysis procedures are described in the above paragraphs and are not redundantly described here again.

In conclusion, the present invention provides a system and a method for health condition monitoring. The inventive system for health condition monitoring includes a wearable device, a portable device and a server. The non-contact ECG acquisition module and the non-contact audio acquisition module used to acquire ECG signals and audio signals are embedded in the wearable device and do not directly contact the skin of the user, which fulfils the requirement of hygiene purpose and makes the wearer feel comfortable to improve the compliance of long term use. The wearable device is designed to provide safety, capability, convenience and comfort to the users. The wearable device also includes a signal processing and analysis module capable of performing QRS detection, HR calculation and ECG derived RR determination. Other signal processing and analysis may be performed on the server side. Particularly, the dual-channel framework consisting of two audio sensors are used to capture the respiratory sound signal and the heart sound signal, and the multiband products based on FFT coefficients are used for the heart sound localization and the heart sound cancellation. The features extracted from ECG signals, the respiratory sound signal and the heart sound signal can be further combined by data fusion analysis to give the final results on condition analysis for the heart and the lung of the user. By means of the portable device and the server, the doctors, caretakers and family members of the user can retrieve data or be informed of situation where the user is in need of care or emergency medical treatments. Therefore, the present invention provides a system and a method for health condition monitoring incorporating ECG and audio sensors, which can be used for the detection, recording, and analysis of signals related to heart and lung functions, anywhere and over a long duration, including treatment response/rehabilitation. Further, the proposed system and method for health condition monitoring may also provide early warning of chronic diseases or alarm for fatigue, stress level etc. Thus, the proposed system and method provide not only current monitoring but also preventative monitoring for health conditions of the user.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A system for health condition monitoring comprising a wearable device, a portable device and a server, the portable device being capable of communicating between the wearable device and the server, the system for health condition monitoring further comprising:
   a non-contact ECG acquisition module embedded in the wearable device for capturing ECG signals from a user wearing the wearable device;
   a non-contact audio acquisition module embedded in the wearable device for capturing a respiratory sound signal and a heart sound signal from the user wearing the wearable device;
   a first signal processing and analysis module embedded in the wearable device and connected with the non-contact ECG acquisition module for receiving and processing the ECG signals, wherein QRS detection, HR (heart rate) calculation and ECG derived RR (respiratory rate) determination are performed in the first signal processing and analysis module, and the first signal processing and analysis module is connected with the non-contact audio acquisition module for receiving and processing the respiratory sound signal and the heart sound signal; and
   a second signal processing and analysis module provided on the server for receiving and processing the ECG signals, the respiratory sound signal and the heart sound signal uploaded by the portable device, wherein heart sound localization, heart sound cancellation, respiratory sound restoration, and sound based RR determination are performed in the second signal processing and analysis module, so as to obtain information for health condition monitoring,
   wherein another QRS detection is performed in the second signal processing and analysis module by a template matching based technique, and the template matching based technique applies adaptive thresholding which is used to remove intervals that exceed a pre-defined percentage.

2. The system for health condition monitoring according to claim 1, wherein the wearable device is a wearable vest, and the portable device is a smart phone or a tablet.

3. The system for health condition monitoring according to claim 1, wherein the non-contact ECG acquisition module and the non-contact audio acquisition module do not directly contact the skin of the user.

4. The system for health condition monitoring according to claim 1, wherein the non-contact ECG acquisition module comprises three or more non-contact ECG sensors.

5. The system for health condition monitoring according to claim 4, wherein the non-contact ECG sensors are located at a top of the manubrium, a left side of the ninth rib, and a right side of the ninth rib when the user is wearing the wearable device.

6. The system for health condition monitoring according to claim 1, wherein the non-contact audio acquisition module comprises two or more non-contact audio sensors for capturing the respiratory sound signal and the heart sound signal.

7. The system for health condition monitoring according to claim 6, wherein the non-contact audio sensor is a MEMS (microelectro-mechanical system) microphone sensor.

8. The system for health condition monitoring according to claim 6, wherein the non-contact audio sensor comprises a bell-shaped acoustic chamber to optimize transfer of sound from the user's body and block external soundwave.

9. The system for health condition monitoring according to claim 1, wherein the wearable device further comprises:
   a microcontroller connected with and managing operations of the non-contact ECG acquisition module, the non-contact audio acquisition module, and the first signal processing and analysis module;
   a data storage connected with the microcontroller for storing the captured signals and processed data; and
   a first transceiver connected with the microcontroller.

10. The system for health condition monitoring according to claim 9, wherein the portable device comprises a second transceiver capable of communicating with the first transceiver of the wearable device.

11. The system for health condition monitoring according to claim 10, wherein the first transceiver and the second transceiver communicate with each other through a Bluetooth protocol.

12. The system for health condition monitoring according to claim 1, wherein the portable device comprises an application capable of communicating with the wearable device and the server for their operations and data transmissions.

13. The system for health condition monitoring according to claim 1, wherein the wearable device comprises an outer layer and an inner layer, and the non-contact ECG acquisition module and the non-contact audio acquisition module are attached to the inner layer and deployed between the outer layer and the inner layer.

14. The system for health condition monitoring according to claim 1, wherein the wearable device comprises a two-section strip made of conductive clothing to ensure secure grounding.

15. The system for health condition monitoring according to claim 1, wherein the ECG signal obtained by the non-contact ECG acquisition module is first filtered to remove the baseline wandering and other noise out of the desired band, and a bandwidth used in filtering the ECG signal is 0.67-150 Hz.

16. The system for health condition monitoring according to claim 1, wherein the QRS detection is performed in the first signal processing and analysis module by a derivative processing based technique.

17. The system for health condition monitoring according to claim 1, wherein the first signal processing and analysis module comprises an adaptive filter with ANC (adaptive noise cancellation) configuration, which is applied to the respiratory sound signal and the heart sound signal to suppress both ambient noise and heart sound simultaneously.

18. The system for health condition monitoring according to claim 1, wherein multiband products based on FFT (fast Fourier transform) coefficients are used for the heart sound localization, the heart sound cancellation, and the respiratory sound restoration.

19. The system for health condition monitoring according to claim 18, wherein the multiband products are calculated by multiplying the FFT coefficients of the desired sub-bands as the following formula:

$$P_{j,k}(\tau) = \prod_{i=j}^{k} |S(\tau, i)|$$

where j is a positive number equal to or greater than 0 which corresponds to the lower bound of the desired sub-band of the heart sound, k is a positive number greater than or equal to j and corresponds to the upper bound of the desired sub-band of the heart sound, $P_{j,k}$ is the multiband product of FFT coefficients from the jth sub-band to the kth sub-band, and $S(\tau, i)$ is the FFT coefficient.

20. The system for health condition monitoring according to claim 18, wherein the respiratory sound restoration is performed by linear prediction using FFT coefficients.

21. The system for health condition monitoring according to claim 18, wherein the sound based RR is estimated from a cleaned respiratory signal after heart sound cancellation by multiplying the squared frequency with the power of its FFT coefficients as the following formulas:

$$Q(\tau, f_n) = |S_{ANC,r}(\tau, f_n)|^2 \cdot f_n^2 \ (n = n_1, n_1 + 1, \ldots n_2)$$

$$P(\tau) = \sum_{n=n_1}^{n_2} Q(\tau, f_n)$$

where $\tau$ is the shift in time, f is the frequency, $n_1$ is a positive number equal to or greater than 0 which corresponds to the lower bound of the desired sub-band of the respiratory sound, $n_2$ is a positive number greater than or equal to $n_1$ and corresponds to the upper bound of the desired sub-band of the respiratory sound, and $S_{ANC,\tau}(\tau,f)$ is the refurbished FFT coefficient.

22. The system for health condition monitoring according to claim 18, wherein a final result of RR is obtained from the ECG derived RR and the sound based RR by a weighted method, where the RR from better signal quality is assigned a heavier weight.

23. A method for health condition monitoring, comprising steps of:
   (a) providing a wearable device, a portable device and a server, the wearable device comprising an embedded non-contact ECG acquisition module, an embedded non-contact audio acquisition module and an embedded first signal processing and analysis module, the portable device being capable of communicating between the wearable device and the server, the server comprising a second signal processing and analysis module;
   (b) capturing ECG signals by the non-contact ECG acquisition module and capturing a respiratory sound signal and a heart sound signal by the non-contact audio acquisition module from the user wearing the wearable device;
   (c) processing the ECG signals, the respiratory sound signal and the heart sound signal by the first signal processing and analysis module to perform QRS detection, HR (heart rate) calculation and ECG derived RR (respiratory rate) determination; and
   (d) processing the ECG signals, the respiratory sound signal and the heart sound signal by the second signal processing and analysis module to perform heart sound localization, heart sound cancellation, respiratory sound restoration, and sound based RR determination, and thus obtaining information for health condition monitoring,
      wherein another QRS detection is performed in the second signal processing and analysis module by a template matching based technique, and the template matching based technique applies adaptive thresholding which is used to remove intervals that exceed a pre-defined percentage.

24. The method for health condition monitoring according to claim 23, further comprising a step of obtaining a final result of RR from the ECG derived RR and the sound based RR by a weighted method, where the RR from better signal quality is assigned a heavier weight.

25. The method for health condition monitoring according to claim 23, wherein the ECG signal obtained by the non-contact ECG acquisition module is first filtered to remove the baseline wandering and other noise out of the desired band, and a bandwidth used in filtering the ECG signal is 0.67-150 Hz.

26. The method for health condition monitoring according to claim 23, wherein the QRS detection is performed in the first signal processing and analysis module by a derivative processing based technique.

27. The method for health condition monitoring according to claim 23, wherein the first signal processing and analysis module comprises an adaptive filter with ANC (adaptive noise cancellation) configuration, which is applied to the respiratory sound signal and the heart sound signal to suppress both ambient noise and heart sound simultaneously.

28. The method for health condition monitoring according to claim 23, wherein multiband products based on FFT (fast Fourier transform) coefficients are used for the heart sound localization and the heart sound cancellation.

29. The method for health condition monitoring according to claim 28, wherein the multiband products are calculated by multiplying the FFT coefficients of the desired sub-bands as the following formula:

$$P_{j,k}(\tau) = \prod_{i=j}^{k} |S(\tau, i)|$$

where j is a positive number equal to or greater than 0 which corresponds to the lower bound of the desired sub-band of the heart sound, k is a positive number greater than or equal to j and corresponds to the upper bound of the desired sub-band of the heart sound, $P_{j,k}$ is the multiband product of FFT coefficients from the jth sub-band to the kth sub-band, and $S(\tau, i)$ is the FFT coefficient.

30. The method for health condition monitoring according to claim 28, wherein the respiratory sound restoration is performed by linear prediction using FFT coefficients.

31. The method for health condition monitoring according to claim 28, wherein the sound based RR is estimated from a cleaned respiratory signal after heart sound cancellation by multiplying the squared frequency with the power of its FFT coefficients as the following formulas:

$$Q(\tau, f_n) = |S_{ANC,r}(\tau, f_n)|^2 \cdot f_n^2 \ (n = n_1, n_1 + 1, \ldots n_2)$$

$$P(\tau) = \sum_{n=n_1}^{n_2} Q(\tau, f_n)$$

where $\tau$ is the shift in time, f is the frequency, $n_1$ is a positive number equal to or greater than 0 which corresponds to the lower bound of the desired sub-band of the respiratory sound, $n_2$ is a positive number greater than or equal to $n_1$ and corresponds to the upper bound of the desired sub-band of the respiratory sound, and $S_{ANC,r}(\tau, f)$ is the refurbished FFT coefficient.

* * * * *